US005760268A

United States Patent [19]
Beisswenger et al.

[11] Patent Number: 5,760,268
[45] Date of Patent: Jun. 2, 1998

[54] PRODUCTION AND USE OF SALTS OF 6, 8-BIS (AMIDINIUMTHIO) -OCTANOIC ACID

[75] Inventors: Thomas Beisswenger, Radebeul; Rainer Gewald, Dresden; Alfred Olbrich, Obertshausen; Horst Bethge, Rodenbach; Frank Hübner, Ober-Ramstadt; Klaus Huthmacher, Gelnhausen; Herbert Klenk, Hanau; Roland Möller, Hammersbach; Stephan Rautenberg, Hanau; Gerhard Sator, Dieburg, all of Germany

[73] Assignee: Asta Medica Aktiengesellschaft, Dresden, Germany

[21] Appl. No.: 786,053

[22] Filed: Jan. 21, 1997

[30] Foreign Application Priority Data

Jan. 19, 1996 [DE] Germany ............ 196 01 787.4

[51] Int. Cl.$^6$ .................................. C07C 335/32
[52] U.S. Cl. .................. 558/5; 549/39; 562/512
[58] Field of Search ........................... 558/5

[56] References Cited

U.S. PATENT DOCUMENTS 2,772,300  11/1956  Wagner ............................ 558/5
2,792,414   5/1957  Walton ............................ 558/5

FOREIGN PATENT DOCUMENTS 1 273 856  2/1962  France .

OTHER PUBLICATIONS

Chemical Abstracts 1962, 57(4), abstract no. 4550d. Abstract of FR 1,273,856, Aug. 1962.

Primary Examiner—Michael G. Ambrose
Attorney, Agent, or Firm—Cushman Darby & Cushman IP Group of Pillsbury Madison & Sutro LLP

[57] ABSTRACT

The invention relates to the production and purification of salts of 6,8-bis(amidiniumthio) octanoic acid, its enantiomers (+)-6,8-bis(amidiniumthio)octanoic acid and (−)-6,8-bis (amidiniumthio)octanoic acid and of the esters of these compounds as well as to their use to produce dihydrolipoic acid and α-lipoic acid.

4 Claims, No Drawings

PRODUCTION AND USE OF SALTS OF 6,8-BIS (AMIDINIUMTHIO) -OCTANOIC ACID

This application claims priority from German Application No. 19601787.4, filed on Jan. 19, 1996, the subject matter of which is incorporated herein by reference.

BACKGROUND OF THE INVENTION

1. Field of the Invention

The invention relates to the production, purification and use of salts of 6,8-bis(amidiniumthio)octanoic acid, its enantiomers and esters of these compounds. 6,8-bis (amidiniumthio)octanoic acid can be converted by hydrolysis of the isothiuronium grouping to 6,8-dimercaptooctanoic acid (also designated as dihydrolipoic acid), which for its part serves as precursor for the pharmacologically active α-lipoic acid.

2. Prior Art

The R enantiomer of α-lipoic acid is a natural substance occurring in practically all animal and vegetable cells. α-lipoic acid is of essential physiological significance as coenzyme in the oxidative decarboxylation of α-ketocarboxylic acids (e.g. pyruvic acid). An important pharmacological indication of racemic α-lipoic acid is diabetic polyneuropathy. In the case of the pure, optical isomers of α-lipoic acid (R and S form, that is, R α-lipoic acid and S α-lipoic acid), in contrast to the racemate the R enantiomer is primarily antiphlogistically and the S enantiomer primarily antinociceptively active (EP 0,427,247, Nov. 8, 1990). Therefore, in addition to the synthesis of racemic α-lipoic acid the synthesis of the pure enantiomers for purposeful pharmaceutical use is also of great importance.

The previously known synthesis methods utilize various variants for the purposeful introduction of mercapto groups onto derivatives or precursors of octanoic acid which are reported in several passages in the literature. (survey articles: J. S. Yadav et al., J. Sci. Ind. Res. 1990, 49, 400; and A. G. Tolstikov et al., Bioorg. Khim. 1990, 16, 1670; L. Dasaradhi et al., J. Chem. Soc., Chem. Commun. 1990, 729; A. S. Gopalan et al., J. Chem. Perkin Trans. 1 1990, 1897; A. S. Gopalan et al., Tetrahedron Lett. 1989, 5705; EP 0.487.986 A2, Nov. 14, 1991; E. Walton et al., J. Am. Chem. Soc. 1955, 77, 1955; D. S. Acker and W. J. Wayne, J. Am. Chem. Soc. 1957, 79, 6483; L. G. Chebotareva and A. M. Yurkevich, Khim.-Farm. Zh. 1980, 14, 92).

Problematic areas in all production variants described are on the one hand multistage synthesis sequences with at times low reaction yields which do not permit an economic operation, or the instability of intermediate stages, which prevents their industrial purification. The required purity for pharmaceutical items can therefore only be achieved by expensive final purification by distillation of the dihydrolipoic acid (6,8-dimercaptooctanoic acid) II and/or by multiple crystallization of the sensitive α-lipoic acid I, which results in considerable product losses. For example, GB 3 996,703 can be cited with its conversion of 6-hydroxy-Δ7-octanoic acid or its esters in which yields of 23 to 51% of theory of dimercaptooctanoic acid II and α-lipoic acid I were obtained by distillation.

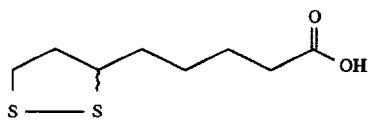

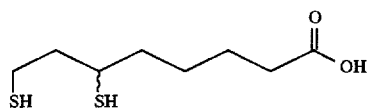

SUMMARY OF THE INVENTION

The invention accordingly has the problem of creating intermediate products for the production of α-lipoic acid which can be readily purified and whose use results in high yields of the final product α-lipoic acid. The invention solves this problem by compounds of the following general formula III

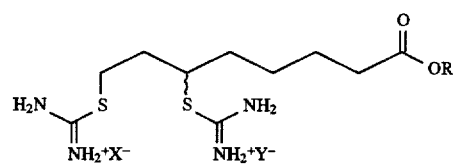

in which R signifies a hydrogen atom or an alkyl group with 1 to 3 carbon atoms and $X^-$ and $Y^-$ are the same or different and signify an anion of a strong acid, preferably a mineral acid, alkyl- or aryl sulfonic acid or carboxylic acid, and their enantiomers.

Examples of especially suitable acids are hydrochloric acid and methylsulfonic acid, naphthalene-1,5-disulfonic acid and terephthalic acid.

The invention also relates to a method of producing compounds of general formula III in which enantiomerically pure or racemic 8-chloro-6-sulfonyloxyoctanoic acid or its $C_1$–$C_3$ alkyl ester are reacted with thiourea.

Preferred sulfonyloxy substituents are methylsulfonyloxy, 4-methylphenylsulfonyloxy- and perfluoroalkylsulfonyloxy groups.

The compounds of formula III can be isolated from the produced reaction mixture out of aqueous solution. The salts present in crystalline or oily form can be obtained by adding sulfonic acids, mineral acids or carboxylic acids.

DETAILED DESCRIPTION OF PREFERRED EMBODIMENTS OF THE INVENTION

It is surprisingly possible to produce racemic or enantiomerically pure dimercaptooctanoic acid II with the method of the invention by protective reaction, which acid can then be oxidized readily and in good yields on account of the purity obtained to racemic or enanziomerically pure α-lipoic acid I.

For example, the following procedure is used in the method of the invention: Racemic 8-chloro-6-hydroxyoctanoic acid or its esters are converted according to the described method of Thursin and Fiymonoto (GB 933, 809) with sulfonic acid chlorides to racemic 8-chloro-6-sulfonyloxyoctanoic acid or its esters. Analogous conversions can also be carried out with 6,8-dihydroxyoctanoic acid and its esters to 6,8-bis(sulfonyloxy)octanoic acid and its esters (Rama Rao et al., Synth. Commun., 17 (1987) 1339). These compounds can then react in solution with thiourea directly to the salts of 6,8-bis(amidiniumthio) octanoic acid or its esters III. However, it is also possible to arrive via enantiomerically pure (+)-8-chloro-6-sulfonyloxyoctanoic acid or (−)-8-chloro-6-sulfonyloxyoctanoic acid or their esters in good yields stereospecifically under complete inversion on the chiral center at the salts of optically active (−)-6,8-bis (amidiniumthio)octanoic acid and (+)-6,8-bis (amidiniumthio)octanoic acid or their [its] esters. The production of the salts of the optically active 6,8-bis (amidiniumthio)octanoic acid takes place thereby in an analogous method as is described for the racemic mixtures.

Potential solvents for these reactions are organic solvents as well as mixtures of them among each other or with water. Examples of suitable organic solvents are: Alkyl alcohols, preferably with chain lengths of 1 to 6, alkyl carboxylic acids, preferably with chain lengths of 2 to 3 and formic acid or the esters of the cited alcohols and carboxylic acids with chain lengths of 2 to 3, saturated and unsaturated linear and cyclic hydrocarbons, preferably alkyl benzenes such as toluene or xylenes, or alkanes such as e.g. pentane or cyclohexane, or halogenated hydrocarbons.

The obtained salts of 6,8-bis(amidiniumthio)octanoic acid or its esters III can be reacted further analogously to the manner known in the literature by alkali hydroxides, alkaline-earth hydroxides or tert. amine base to racemic or enantiomerically pure 6,8-dimercaptooctanoic acid II (Organikum 12th edition (1973), p. 223, VEB Deutscher Verlag der Wissenschaften, Berlin). Subsequently, (–)-6,8-dimercaptooctanoic acid II and (+)-6,8-dimercaptooctanoic acid II or R-α-lipoic acid I and S-α-lipoic acid I can be obtained thereby in excellent optical purity (e.e.>99%, chiral HPLC) as compounds which can be used pharmaceutically.

The present invention makes it possible to make accessible the salts of the racemates and of the enantiomers of 6,8-bis(amidiniumthio)octanoic acid as well as the esters of these compounds in a simple and economical manner in high purity. This is explained in detail in the following examples.

The purity of the optical isomers was determined by the specific optical amounts of rotation. In addition, the relative contents of the optical isomers of 8-chloro-6-hydroxyoctanoic acid and of α-lipoic acid IIa/b were investigated by HPLC on optically active columns and determined with a detection limit of >0.5%.

EXAMPLE 1

28.7 g (0.10 mole) 8-chloro-6-methane sulfonyloxyoctanoic acid methylester (286.453) were dissolved in 50 ml ethanol and 85 ml toluene and 15.2 g (0.20 mole) thiourea added. The mixture was heated for 4 h until reflux and then distilled to an overhead temperature of 110° C. 130 ml water were added to the reaction mixture, cooled off and the phases separated. The aqueous phase contained 6,8-bis (amidiniumthio)octanoic acid methylester chloride methylsulfonate, which was compounded with 2.0 ml concentrated hydrochloric acid and distilled 2 h until an overhead temperature of 100° C. The solution was concentrated by evaporation and finally dried in a high vacuum. The remaining oil contained 6,8-bis(amidiniumthio)octanoic acid chloride methylsulfonate.

Yield: 33.0 g (78% of theory) [424.98]6,8-bis (amidiniumthio) octanoic acid chloride methylsulfonate $C_{11}H_{25}N_4O_5S_3Cl$ Elementary analysis: calc.: C 31.09 H 5.93 N 13.18 S 22.63 Cl 8.3 O 18.82 obs.: C 29.69 H 6.15 N 12.16 S 21.86 Cl 8.5; 2.5% $H_2O$ IR: 1710 s, 1660 s, 1550 m, 1430 s, 1240 m, 1200/1170 s, 1050 s, 790 s.

$^1$H-NMR $d_6$DMSO: 12.0 s (1H) COOH; 9.25 s (8H) $NH_2$; 3.97 m (1H) CH—S; 3.32 m (2H) $CH_2$—S; 2.46 s (3H) $SO_3CH_3$; 2.25 m (2H) $SCH_2C\underline{H}_2$; 2.00 m (2H)$CH_2$; 1.78/1.58 m (2H $CH_2$; 1.53 m (2H)$CH_2$; 1.40 m (2H) $CH_2$;

$^{13}$C—NMR $d_6$-DMSO: 174.25 COOH; 169.70/169.19 S—C $(NH_2)_2$; 45.32 S—CH; 39.83 $CH_3SO_3$; 33.72; 33.45; 32.84; 27.07; 25.32; 24.14.

6,8-bis(amidiniumthio)octanoic acid methylester chloride methylsulfonate $^1$H-NMR $d_6$-DMSO: 3.92 m (1H) CH—S; 3.57s(3H) $OCH_3$; 3.27 m (2H) $CH_2$—S; 2.45 s (3H) $SO_3CH_3$; 2.4 m (2H) $SCH_2C\underline{H}_2$; 1.97 m (2H) $CH_2$; 1.76/1.52 m (2H) $CH_2$; 1.50 m (2H) $CH_2$; 1.35 m (2H) $CH_2$.

EXAMPLE 2

28.7 g (0.10 mole) 8-chloro-6-methane sulfonyloxyoctanoic acid methylester were dissolved in 50 ml ethanol, 85 ml toluene and 10 ml water and 15.2 g (0.20 mole) thiourea added. The mixture was heated for 4 hours until reflux and then distilled to an overhead temperature of 110° C. 130 ml water were added to the reaction mixture, cooled off and the phases separated. The solution was concentrated by evaporation and finally dried in a high vacuum. The remaining oil contained 6,8-bis(amidiniumthio)octanoic acid chloride methylsulfonate.

Yield: 34.0 g (80% of theory) [424.98]6,8-bis (amidiniumthio) octanoic acid chloride methylsulfonate

EXAMPLE 3

28.7 g (0.10 mole) 8-chloro-6-methane sulfonyloxyoctanoic acid methylester dissolved in 10 ml toluene was dissolved in 50 ml ethanol, 85 ml toluene and 10 ml water and 15.2 g (0.20 mole) thiourea added. The mixture was heated for 4 hours until reflux and then distilled to an overhead temperature of 110° C. 130 ml water were added to the reaction mixture, cooled off and the phases separated. The aqueous phase was compounded with a solution of 33.2 g (0.10 mole) 1,5-naphthalene disulfonic acid disodium salt dissolved in 100 ml water. The developing suspension was agitated at room temperature overnight and the salt filtered off. The salt was then dried at 70° C. in a vacuum. 6,8-bis (amidiniumthio)octanoic acid naphthalene-1,5-disulfonate was obtained.

Yield: 49.4 g (85% of theory) 6,8-bis(amidiniumthio) octanoic acid naphthalene-1,5-disulfonate [580.70].

$C_{20}H_{28}N_4O_8S_4$

Elementary analysis: calc.: C 41.37 H 4.86 N 9.65 S 22.08 O 22.04 obs.: C 41.36 H 4.80 N 9.58 S 22.17

IR: 3170 s, 1730 s, 1660 s, 1440 m, 1410 s, 1210 m, 1180/1150 s, 1030 s, 810 s, 770 s.

$^1$H-NMR $d_6$-DMSO: 12.0 s (1H) COOH; 9.02 s (8H) $NH_2$; 88 d (2H) CH=; 8.00 d (2H) CH=; 7.45 t (2H) CH=; 3.80 m (1H) CH—S; 3.20 m (2H) $CH_2$—S; 2.22 m (2H) $SCH_2C\underline{H}_2$; 1.95 m (2H) $CH_2$; 1.72/1.55 m (2H) $CH_2$; 1.50 m (2H) $CH_2$; 1.34 m (2H) $CH_2$.

EXAMPLE 4

28.7 g (0.10 mole) 8-chloro-6-methane sulfonyloxyoctanoic acid methylester were dissolved in 50 ml ethanol, 85 ml toluene and 10 ml water and 15.2 g (0.20 mole) thiourea added. The mixture was heated for 4 hours until reflux and then distilled to an overhead temperature of 110° C. 130 ml water were added to the reaction mixture, cooled off and the phases separated. The aqueous phase was compounded with a solution of 21 g (0.10 mole) terephthalic acid disodium salt dissolved in 100 ml water. The developing suspension was agitated 4 h at room temperature and the salt filtered off. The salt was then dried at 70° C. in a vacuum. 6,8-bis (amidiniumthio)octanoic acid terephthalate was obtained.

Yield: 49.4 g (85% of theory) 6,8-bis(amidiniumthio) octanoic acid terephthalate [458.55]

Elementary analysis: calc.: C 47.15 H 5.72 N 12.22 S 13.98 O 20.93 obs.: C 47.53 H 5.78 N 11.13 S 13.03

IR (KBr): 3250 s, 1690 s, 1580 s, 1430 m, 1410 s, 1370 m, 1290 s $^{1}$-H-NMR D$_2$O: 7.70 s (4H) Ph—H; 4.55 s COOH/H$_2$O/NH$_2$; 3.50 m (1H) CH—S; 3.05 m (2H) CH$_2$—S; 2.02 m (2H) SCH$_2$CH$_2$; 1.95/1.90 m (2H) CH$_2$; 1.60/1.55 m (2H) CH$_2$; 1.37 m (2H) CH$_2$; 1.25 m (2H) CH$_2$

EXAMPLE 5

36.2 g (0.10 mole) 8-chloro-6-(4-methylphenylsulfonyloxy)octanoic acid methylester (362.453) were dissolved in 50 ml ethanol, 85 ml toluene and 10 ml water and 15.2 g (0.20 mole) thiourea added. The mixture was heated for 4 hours until reflux and then distilled to an overhead temperature of 110° C. 130 ml water were added to the reaction mixture, cooled off and the phases separated. The aqueous phase, which contained 6,8-bis(amidiniumthio)octanoic acid chloride 4-methylphenylsulfonate, was compounded with a solution of 33.2 g (0.10 mole) 1,5-naphthalene disulfonic acid disodium salt dissolved in 100 ml water. The developing suspension was agitated 4 h at room temperature and the salt filtered off. The salt was then dried at 70° C. in a vacuum. 6,8-bis(amidiniumthio)octanoic acid naphthalene-1,5-disulfonate was obtained.

Yield: 58.2 g (91% of theory) 6,8-bis(amidiniumthio) octanoic acid naphthalene-1,5-disulfonate [580.70]

EXAMPLE 6

34.6 g (0.10 mole) 6,8-bis(methylsulfonyloxy)octanoic acid methylester (346.4) were dissolved in 50 ml ethanol, 85 ml toluene and 10 ml water and 15.2 g (0.20 mole) thiourea added. The mixture was distilled to an overhead temperature of 110° C. and then heated 4 h until reflux. 130 ml water were added to the reaction mixture, cooled off and the phases separated. The aqueous phase, which contained 6,8-bis(amidiniumthio)octanoic acid dimesylate, was compounded with a solution of 33.2 g (0.10 mole) 1,5-naphthalene disulfonic acid disodium salt dissolved in 100 ml water. The developing suspension was agitated 4 h at room temperature and the salt filtered off. The salt was then dried at 70° C. in a vacuum. 6,8-bis(amidiniumthio)octanoic acid naphthalene-1,5-disulfonate was obtained.

Yield: 58.2 g (91% of theory) 6,8-bis(amidiniumthio) octanoic acid naphthalene-1,5-disulfonate [580.70]

EXAMPLE 7

21.25 g (0.0366 mole) 6,8-bis(amidiniumthio)octanoic acid naphthalene-1,5-disulfonate were dissolved in 200 ml ethanol and 200 ml water and compounded at 70° C. with 7.62 g (0.0366 mole) barium chloride dissolved in 100 ml water. The developing suspension was agitated 4 hours at 70° C. and the solid matter filtered off. The liquid phase was concentrated by evaporation and yielded a saline, oily residue. The latter was thoroughly agitated with 50 ml ethanol at 60° C. and filtered off. The ethanolic solution was evaporated to dryness and freed of solvent in a high vacuum.

Yield: 13.2 g (0.036 mole) 70% of theory 6,8-bis (amidiniumthio)octanoic acid dichloride [365.34]

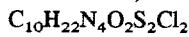

Elementary analysis: calc.: C 32.88 H 6.07 N 15.34 S 17.55 Cl 19.4 0 8.76 obs.: C 32.49 H 6.48 N 14.92 S 17.24 Cl 19.19; 1.13 % H$_2$O IR: 1710 s, 1640 s, 1530 m, 1430 s, 1240 m, 1200/1180 s, 1070 s $^{1}$H-NMR d$_6$DMSO: 12.0 s (1H) COOH; 9.3 s (8H) NH$_2$; 4.12 m (1H) CH—S; 3.40 m (2H) CH$_2$—S; 2.27 m (2H) SCH$_2$CH$_2$; 2.00 m (2H) CH$_2$; 1.80/1.56 m (2H) CH$_2$; 1.53 m (2H) CH$_2$; 1.43/1.36 m (2H) CH$_2$; $^{13}$C-NMR d$_6$-DMSO: 174.13 COOH; 169.69/169.22 S—C(NH$_2$)$_2$; 45.10 S—CH; 33.96; 33.35; 32.58; 26.92; 25.25; 24.02

EXAMPLE 8

21.25 g (0.0366 mole) 6,8-bis(amidiniumthio)octanoic acid naphthalene-1,5-disulfonate were dissolved in 200 ml ethanol and 200 ml water and compounded at 70° C. with 7.62 g (0.0366 mole) barium methane sulfonate dissolved in 100 ml water. The developing suspension was agitated 4 hours at 70° C. and the solid matter filtered off. The liquid phase was concentrated by evaporation and yielded a saline, oily residue. The latter was thoroughly agitated with 50 ml ethanol at 60° C. and filtered off. The ethanolic solution was evaporated to dryness and freed of solvent in a high vacuum.

Yield: 13.2 g (0.036 mole) 98% of theory 6,8-bis (amidiniumthio)octanoic acid bis(methane sulfonate) [484.62]

EXAMPLE 9

58.0 g (0.10 mole)6,8-bis(amidiniumthio)octanoic acid naphthalene-1,5-disulfonate (580.70 were suspended in 100 ml water and 40 ml (0.50 mole) sodium hydroxide solution (50%) added dropwise within 20 min. A suspension was obtained which was heated 1 h to 40° C. and subsequently diluted with 550 ml water. The solution was acidified with 62.5 g (0.75 mole) concentrated hydrochloric acid and extracted 3 times with 100 ml toluene. The combined organic phases were concentrated by evaporation in a vacuum to dryness.

Yield: 20.2 g (97% of theory) 6,8-dimercaptooctanoic acid

EXAMPLE 10

20.0 g 6,8-dimercaptooctanoic acid were dissolved in 100 ml aqueous sodium hydroxide solution (0.1 mole) and oxidized with hydrogen peroxide solution. After the addition of 200 ml toluene the mixture was acidified with hydrochloric acid under agitation to a pH of 1 and the organic phase isolated.

Yield: The organic phase contained α-lipoic acid quantitatively

EXAMPLE 11

28.7 g (0.10 mole) (+)-8-chloro-6-methane sulfonyloxyoctanoic acid methylester [α]$_D^{20}$=32.90° (c=1.0; ethanol) [286.453] were dissolved in 50 ml ethanol and 85 ml toluene and 15.2 g (0.20 mole) thiourea added. The mixture was heated for 4 h until reflux and then distilled to an overhead temperature of 110° C. 130 ml water were added to the reaction mixture, cooled off and the phases separated. The aqueous phase contained (+)-6,8-bis(amidiniumthio) octanoic acid methylester chloride methylsulfonate, which was compounded with 2.0 ml concentrated hydrochloric acid and distilled 2 h until an overhead temperature of 100° C. The solution, which contained the (+)-6,8-bis (amidiniumthio)octanoic acid chloride methylsulfonate, was compounded with a solution of 33.2 g (0.10 mole) 1,5-naphthalene disulfonic acid disodium salt dissolved in 100 ml water. The developing suspension was agitated 4 h at room temperature and the salt filtered off. The salt was subsequently dried at 70° C. in a vacuum. (+)-6,8-bis (amidiniumthio)octanoic acid naphthalene-1,5-disulfonate was obtained.

Yield: 52.8 g (91% of theory) (+)-6,8-bis(amidiniumthio) octanoic acid naphthalene-1,5-disulfonate [580.70]

$C_{20}H_{28}N_4O_8S_4$

Elementary analysis: calc.: C 41.37 H 4.86 N 9.65 S 22.08 O 22.04 obs.: C 41.17 H 4.77 N 9.63 S 22.13

IR: 3170 s, 1730 s, 1660 s, 1440 m, 1410 s, 1210 m, 1180/1150 s, 1030 s, 810 s, 770 s $^1$H-NMR $d_6$-DMSO: 12.0 s (1H) COOH; 9.2 s (8H) NH$_2$; 8.90 d (2H) CH=; 7.97 d (2H) CH=; 7.43 t (2H) CH=; 3.78 m (1H) CH—S; 3.18 m (2H) CH$_2$—S; 2.21 m (2H) SCH$_2$CH$_2$; 1.94 m (2H) CH$_2$; 1.70/1.55 m (2H) CH$_2$; 1.51 m (2H) CH$_2$; 1.37 m (2H) CH$_2$ $[\alpha]_D^{20}$=+5.7° (c=1.2; DMSO)

EXAMPLE 12

58.0 g (0.10 mole) (+)-6,8-bis(amidiniumthio)octanoic acid naphthalene-1,5-disulfonate [580.70] were suspended in 100 ml water while rendering the mixture inert under nitrogen and 40 g (0.50 mole) sodium hydroxide solution (50%) added dropwise within 20 min. A suspension was obtained which was heated 1 h to 40° C. The mixture was then diluted with 550 ml water. The solution was acidified with 62.5 g (0.75 mole) concentrated hydrochloric acid and extracted 3 times with 100 ml toluene. The combined organic phases were concentrated to dryness in a vacuum.

Yield: 20.2 g (97% of theory) (−)-6,8-dimercaptooctanoic acid

Enantiomeric purity ee.:>99% $[\alpha]_D^{20}$=−13.5° (c=1.0; ethanol)

EXAMPLE 13

28.7 g (0.10 mole) (+)-8-chloro-6-methane sulfonyloxy-octanoic acid methylester, $[\alpha]_D^{20}$=+32.8° (c=1.0; ethanol) [286.453] were dissolved in 50 ml ethanol and 85 ml toluene and 15.2 g (0.20 mole) thiourea added. The mixture was heated 4 h to reflux and then distilled to an overhead temperature of 110° C. 130 ml water were added to the reaction mixture, cooled off and the phases separated. The aqueous phase contained (+)-6,8-bis(amidiniumthio) octanoic acid methylester chloride methylsulfonate, which was compounded with 2.0 ml concentrated hydrochloric acid and distilled 2 h to an overhead temperature of 100° C. The solution, which contained (+)-6,8-bis(amidiniumthio) octanoic acid chloride methylsulfonate, was compounded with a solution of 33.2 g (0.10 mole) 1,5-naphthalene disulfonic acid disodium salt dissolved in 100 ml water. The developing suspension was agitated 4 h at room temperature and the salt was subsequently dried at 70° C. in a vacuum. (+)-6,8-bis(amidiniumthio)octanoic acid naphthalene-1,5-disulfonate was obtained.

Yield: 52.8 g (91% of theory) (+)-6,8-bis(amidiniumthio) octanoic acid naphthalene-1,5-disulfonate [580.70]

$C_{20}H_{28}N_4O_8S_4$

Elementary analysis: calc.: C 41.37 H 4.86 N 9.65 S 22.08 O 22.04 obs.: C 41.13 H 4.73 N 9.59 S 22.19

IR: 3170 s, 1730 s, 1660 s, 1440 m, 1410 s, 1210 m, 1180/11L50 s, 1030 s, 810 s, 770 s $^1$H-NMR $d_6$-DMSO: 12.0 s (1H) COOH; 9.2 s (8H) NH$_2$; 8.90 d (2H) CH=; 7.97 d (2H) CH=; 7.43 t (2H) CH=; 3.78 m (1H) CH—S; 3.18 m (2H) CH$_2$—S; 2.21 m (2H) SCH$_2$CH$_2$; 1.94 m (2H) CH$_2$; 1.70/1.55 m (2H) CH$_2$; 1.51 m (2H) CH$_2$; 1.37 m (2H) CH$_2$ $[\alpha]_D^{20}$=+5.6° (c=1.0; DMSO)

EXAMPLE 14

58.0 g (0.10 mole) (+) -6,8-bis(amidiniumthio)octanoic acid naphthalene-1,5-disulfonate [580.70] were suspended in 100 ml water while rendering the mixture inert under nitrogen and 40 g (0.50 mole) sodium hydroxide solution (50%) added dropwise within 20 min. A suspension was obtained which was heated 1 h to 40° C. The mixture was then diluted with 550 ml water. The solution was acidified with 62.5 g (0.75 mole) concentrated hydrochloric acid and extracted 3 times with 100 ml toluene. The combined organic phases were concentrated to dryness in a vacuum.

Yield: 20.2 g (97% of theory) (−)-6,8-dimercaptooctanoic acid

Enantiomeric purity ee.:>99% $[\alpha]_D^{20}$=−13.7° (c=1.5; ethanol)

EXAMPLE 15

58.0 g (0.10 mole) (−)-6,8-bis(amidiniumthio)octanoic acid naphthalene-1,5-disulfonate [580.70] were suspended in 100 ml water and 40 g (0.50 mole) sodium hydroxide solution (50%) added dropwise within 20 min. A suspension was obtained which was heated 1 hr to 40° C. The mixture was then diluted with 550 ml water. The solution was acidified with 62.5 g (0.75 mole) concentrated hydrochloric acid and extracted three times with 100 ml toluene. The toluene extracts were compounded under agitation with 100 ml aqueous sodium hydroxide solution (0.1 mole) and oxidized with hydrogen peroxide solution. The mixture was then acidified with hydrochloric acid under agitation to a pH of 1 and the organic phase isolated. The organic phase was concentrated by evaporation to dryness and dried in a vacuum.

Yield: 19.2 g (93% of theory) S-(−)-α-lipoic acid

Enantiomeric purity ee.:>99% $[\alpha]_D^{20}$=−119° (c=1; ethanol)

Melting point: 49°–50° C.

What is claimed is:

1. A compound of formula III:

$$\text{(III)}$$

in which R signifies a hydrogen atom and X$^-$ and Y$^-$ are the same or different and signify an anion of a mineral acid, alkyl- or aryl sulfonic acid or carboxylic acid, or an enantiomer thereof.

2. A method of producing a compound according to claim 1 in which an enantiomerically pure or racemic 8-chloro-6-sulfonyloxyoctanoic acid or a $C_1$-$C_3$-alkyl ester thereof is reacted with thiourea, and in the case of $C_1$-$C_3$-alkyl ester further treated with hydrochloric acid.

3. The method according to claim 2 in which a methylsulfonyloxy-, 4-methylphenylsulfonyloxy-, or perfluoroalkylsulfonyloxy group is used as sulfonyloxy substituent.

4. The method according to claim 2 or 3 in which a compound of formula III according to claim 1 is isolated in crystalline form or as an oil from aqueous solution as a salt of a sulfonic acid, a mineral acid or a carboxylic acid.

* * * * *